United States Patent [19]
Trend et al.

[11] Patent Number: 5,474,743
[45] Date of Patent: Dec. 12, 1995

[54] CATION-SENSING COMPOSITE STRUCTURE AND COMPOUNDS FOR USE THEREIN

[75] Inventors: John E. Trend, St. Paul; Cary A. Kipke, Woodbury; Mitchell A. Rossman, Mendota Heights, all of Minn.; Masao Yafuso, Lake Forest; Sanjay L. Patil, Irvine, both of Calif.

[73] Assignee: Minnesota Mining and Manufacturing Company, St. Paul, Minn.

[21] Appl. No.: 140,257

[22] Filed: Oct. 21, 1993

[51] Int. Cl.$^6$ .......................... G01N 21/64; G01N 21/77; C07D 419/02
[52] U.S. Cl. .................. 422/82.07; 540/469; 436/172
[58] Field of Search .................... 436/172, 166, 436/140; 422/82.07, 82.08, 82.11; 540/468, 469; 558/44

[56] References Cited

U.S. PATENT DOCUMENTS

| | | | |
|---|---|---|---|
| 4,504,368 | 3/1985 | Delton et al. | 204/1 |
| 4,577,109 | 3/1986 | Hirschfeld | 250/461 |
| 4,762,799 | 8/1988 | Seitz et al. | 436/79 |
| 4,808,539 | 2/1989 | Chapoteau et al. | 436/74 |
| 4,822,746 | 4/1989 | Walt | 436/528 |
| 4,830,013 | 5/1989 | Maxwell | 128/637 |
| 4,859,606 | 8/1989 | Cram et al. | 436/79 |
| 4,929,561 | 5/1990 | Hirschfeld | 436/116 |
| 5,037,615 | 8/1991 | Kane | 422/82 |
| 5,045,475 | 9/1991 | Chapoteau et al. | 436/74 |
| 5,096,831 | 3/1992 | Chapoteau et al. | 436/74 |
| 5,136,033 | 8/1992 | Masilamani et al. | 540/468 |
| 5,154,890 | 10/1992 | Mauze et al. | 422/82 |
| 5,162,525 | 11/1992 | Masilamani et al. | 540/468 |
| 5,176,882 | 1/1993 | Gray et al. | 422/82.07 |
| 5,187,103 | 2/1993 | Czech et al. | 436/79 |

FOREIGN PATENT DOCUMENTS

| | | |
|---|---|---|
| 3202779A1 | 8/1983 | Germany. |
| WO92/07899 | 5/1992 | WIPO. |

OTHER PUBLICATIONS

"Synthesis and Characterization of a new Fluorescent probe for Measuring Potassium", Golchini et al, Am. Phys, F438–F443, vol. 258, Feb. 1990.

J. M. Lehn and J. F. Sauvage, "[2]-Cryptates: Stability and Selectivity of Alkali and Alkaline–Earth Macrobicyclic Complexes", *J. Am. Chem. Soc.*, 97, 6700–07 (1975).

D. Landini, F. Montanari and F. Rolla, "Phase–Transfer Catalyst: Synthesis and Catalytic Activity of a Tricyclohexyl [2.2.2]cryptand (Perhydrotribenzohexaoxadiaza[8.8.8] eicosane)", *Synthesis*, 223–25 (1978).

*Organic Synthesis, Collective* vol. 5, 49–51 (1973).

H. Gross, A Reiche and G. Matthey, *Chem. Ber.*, 96, 308–13 (1963)(translation).

V. Balaiah, T. R. Seshadri and V. Venkateswarlu, "Visible Fluorescence and Chemical Constitution of Compounds of the Benzopyrone Group. Part III. Further Study of Structural Influences in Coumarins", *Proc. Indian Acad. Sci.*, 16A, 68–82 (1942).

W. Borsche and P. Hahn–Weinheimer, *Chem. Ber.*, 85, 198–202 (1952)(translation).

K. Fukui and M. Nakayama, "Synthetic Studies of Sesamol Derivatives. I. A New Synthesis of Ayapin", *Bull. Chem. Soc. Japan*, 35, 1321–23 (1962).

E. Bissell, "An Improved Synthesis of Certain 3–Ethoxycarbonylcoumarins", *Synthesis*, 846–48 (1982).

E. Kaiser, R. L. Colescott, C. D. Bossinger, P. I. Cook, "Color Test for Detection of Free Terminal Amino Groups in the Solid–Phase Synthesis of Peptides", *Anal. Biochem.*, 34, 595 (1970).

V. K. Sarin, S..B. Kent, J. P. Tam and R. B. Merrifield, "Quantitive Monitoring of Solid–Phase Peptide Synthesis by the Ninhydrin Reaction", *Anal. Biochem.*, 117, 147 (1981).

H. He, H. Li, G. Mohr, B. Kovacs, T. Werner and O. Wolfbeis, "Novel Type of Ion–Selective Fluorosensor Based on the Inner Filter Effect: An Optrode for Potassium", *Anal. Chem.*, 65, 123–127 (1993).

Y. Kawabata, T. Imasama and N. Ishibashi, "Fluorimetric Determination of Potassium Ion Using Hexadecyl–acridine Orange Immobilized on a Poly(vinyl chloride) Membrane Attached to a Flow–through Cell", *Analytica Chimica Acta*, 255, 97–101 (1991).

*Primary Examiner*—Robert J. Warden
*Assistant Examiner*—N. Bhat
*Attorney, Agent, or Firm*—Gary L. Griswold; Walter N. Kirn; David G. Burleson

[57] ABSTRACT

A fluorescent ionophoric compound comprises a cryptand portion and a coumarin portion substituted at the 3-position with an electron withdrawing or polarizable group. The compound, which exhibits good photostability, can be incorporated into cation-sensing composite structures useful in biological and environmental testing, which can be used with conventional glass optics, by means of convenient points of covalent attachment.

25 Claims, No Drawings

CATION-SENSING COMPOSITE STRUCTURE AND COMPOUNDS FOR USE THEREIN

FIELD OF THE INVENTION

This invention describes fluorescent coumarocryptand ionophores, and methods for synthesis and use thereof. These ionophores are useful as cation-detecting agents. This invention also describes cation-sensing composite structures which incorporate these coumarocryptand ionophores and which are useful in continuous sensing applications.

BACKGROUND OF THE INVENTION

The measurement of concentrations of ionic components in various fluids is an increasingly common procedure. Some environmental testing procedures involve frequent, and sometimes continuous, determinations of the concentrations of one or more metal ions, especially ions of heavy metals. Similarly, certain medical diagnostic and treatment procedures involve frequent, and sometimes continuous, determinations of the concentrations of one or more ions in one or more bodily fluids of a patient. The necessity for better continuous testing methods has become increasingly apparent. Continuous, real time monitoring of serum potassium ion ($K^+$) levels in blood and other bodily fluids is highly desirable, especially during heart bypass surgical procedures.

Several methods have been reported for the measurement of metal cation concentrations. Examples include detection based on ion exchange membranes; spectrophotometric and fluorometric techniques involving the presence of reagents; wet electrodes; and ionophore-based detection. Some of these are not effective in determining alkali metal ion concentrations, however. Among methods commonly used to determine alkali metal ion concentrations are those which monitor various optical properties. Of these, techniques measuring fluorescence are preferred to those based on other spectroscopic observations. Methods using fluorescence enjoy sensitivity and operational advantages rooted in the intrinsic separation of the excitation (probe) and emission (signal) wavelengths. Compounds useful for in vitro cation concentration determinations have been described in, for example, U.S. Pat. No. 4,808,539.

The use of fiber optic chemical sensors to create in vivo systems is well known. For instance, incorporation of a chemical sensor into a fiber optic waveguide such that the sensor will interact with the analyte and detect optical changes is known from U.S. Pat. No. 4,577,109. Use of a tethered pair of fluorescence energy transfer indicators as a chemical sensor in a fiber optic waveguide is known from U.S. Pat. No. 5,037,615. Use of fiber optics to monitor the signal generated by a substrate-immobilized fluorescer that is sufficiently close to an absorber substance to allow resonant energy transfer energy to occur is known from U.S. Pat. Nos. 4,929,561. 4,822,746 discloses the use of fiber optics to detect fluorescence in a system comprising fluorogenic substances in combination with light-absorbing ligands and light-absorbing complexes. Detection of fluorescence by fiber optics in a system comprising a solution containing a polymeric cationic material and a fluorescent anionic material in contact, through a semipermeable membrane, with a mobile ionophore selective toward a particular alkali metal ion is taught by U.S. Pat. No. 4,762,799.

Several fluorimetric methods that could potentially be adapted for in vivo/ex vivo use have been described. For instance, fluorescent probes consisting of rhodamine ester and merocyanine 540 as fluorophores and valinomycin as an ionophore are known. More recently, a fiber optic sensor employing 2,2-bis[3,4-(15-crown-5)-2-nitrophenylcarbamoxymethyl]tetradecanol-14, with Rhodamine-B attached as a fluorophore, to selectively complex potassium ions has been described. This device is specifically designed for in vivo use. However, it is subject to several limitations including potential out-migration of the dye-ionophore species; control of permeability (through crosslink density) must be determined at the time of polymerization; potential instability toward hydrolysis of the ester linkage; and lack of control of the net charge of the matrix which, if uncompensated, could lead to Donnan exclusion of the ions to be sensed.

Several of these methods have been beset by deficiencies in sensitivity and selectivity toward alkali metal ions at physiological concentrations, particularly in aqueous media at physiological pH. One method that overcomes some of the selectivity problems is based on the use of cryptands to selectively complex with potassium, described in, for example, DE 3202779 A1. The sensitivity of that method is limited, however, since detection is based on optical absorption. Also, the process must be carried out in an organic solvent in the presence of an organic base, thus not lending itself to continuous blood or fluid determinations. In U.S. Pat. No. 5,162,525 are described a family of fluorogenic ionophores based on a 4-methyl-coumarin moiety united with various cryptands. The [2.2.2] cryptand derivative,

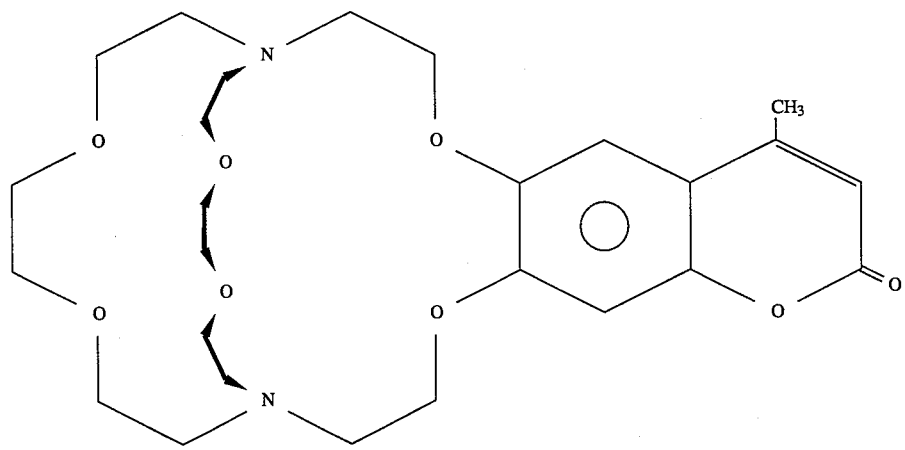

which is selective for the potassium ion, does not suffer from the aforementioned selectivity limitations and allows for potassium ion concentration determination by fluorescence.

SUMMARY OF THE INVENTION

Briefly, the present invention provides a fluorescent ionophoric compound having the general formula

A wherein
m and n are independently 0 or 1,
R is an electron withdrawing or polarizable group, and
Z is oxygen or N—R" where R" is H or a $C_1$ to $C_4$ alkyl group,
the compound having an absorbance maximum in the range of 350 to 440 nm.

In another aspect, the present invention provides a bis-substituted aromatic compound having the formula

B wherein Y is hydrogen or an aldehyde group and L is selected from the group consisting of chlorine, bromine, and iodine, and alkylsulfonate and arylsulfonate groups.

In yet another aspect, the present invention provides a cation-sensing composite structure comprising a substrate having covalently bound thereto, either directly or by means of a linking group, a fluorescent ionophoric compound having the general formula shown above (formula A) wherein R comprises at least one functionality capable of chemical reaction with a functional group on at least one of the substrate or the linking group. (By "directly bound" is meant a covalent bond between an atom of R from formula A and an atom on the surface of the substrate.)

In a further aspect, the present invention provides a method for preparing the above fluorescent ionophoric compound comprising the steps:
a) condensing
 1) the above bis-substituted aromatic compound (formula B), with
 2) an approximately equimolar amount of one of (a) and (b):
  (a) a bifunctional methylene compound of the general formula

A—CH$_2$—B wherein
   A is R, as previously defined, or a direct precursor thereof, and
   B is selected from the group consisting of carboxyl and nitrile groups,
  optionally in the presence of an effective amount of catalyst, with the limitation that Y of the above bis-substituted aromatic compound is an aldehyde group;
  (b) an olefinic compound of the general formula wherein
   D and E are independently selected from the group consisting of A and B,
   G is a group containing an atom with at least one lone pair of electrons, and
   R' is hydrogen or a lower alkyl group (i.e., one with 1 to 4 carbon atoms),
  in the presence of a Lewis acid, with the limitation that Y of the above bis-substituted aromatic compound is hydrogen;
to provide a leaving group-terminated bis-ethoxy coumarin derivative, and
b) generating the cryptand portion of the ionophoric compound by reacting the derivative from a) with an approximately equimolar amount of a diaza crown compound to provide the fluorescent ionophoric compound.

In a still further aspect, the present invention provides a method of determining the presence and concentration of cations comprising the steps:
(a) providing a sensing composite structure as disclosed above comprising a fluorescent ionophore in contact with a metal ion-containing medium which is capable of ion transport and allowing or providing a means for the ions to diffuse to the sensing composite structure to form an equilibrium complex with the fluorescent ionophore of the sensing composite structure, wherein the ionophoric complex, when exposed to light of a wavelength range centered around $\lambda_1$, is capable of emitting light of a wavelength range centered around $\lambda_2$, wherein $\lambda_2$ is at least 10 nm greater than $\lambda_1$, and $\lambda_1$ is between 350 and 440 nm;
(b) interrogating the complex with light having wavelength $\lambda_1$ for a time sufficient for the complex to emit visible light of wavelength $\lambda_2$ which is collected and detected; and (c) optionally, correlating the emitted light with the concentration of metal ions to determine the metal ion concentration.

In this application, unless otherwise specified, the following definitions apply:

"group" or "compound" or "moiety" means a chemical species that allows for substitution by conventional substituents which do not interfere with the desired product;

"coumarocryptand" means a coumarin moiety to which has been benzo-fused, at the 6 and 7 positions, a cryptand moiety;

"alkyl" means a straight or branched organic group having from 1 to 30 carbon atoms in the longest chain;

"aryl" means a ring or fused ring system having from 5 to 15 carbon or hetero atoms in the ring or rings;

"aromatic" means a ring or fused ring system, having from 5 to 15 carbon or hetero atoms in the ring or rings, the electrons of the rings being delocalized;

"carboxyl" means a carboxylic acid group or a derivative thereof and includes, for example, acid halides, azides, amides, imidazoleamides, esters, and nitriles; and "interrogate" means to expose to a source of excitation radiation.

The present invention teaches a coumaro[2.2.2]cryptand ionophore that is, in the absence of $Pb^{+2}$ or $Ba^{+2}$, highly selective for $K^+$, as well as other coumarocryptands that are highly selective for other mono and divalent cations. Advantageously, the [2.2.2]coumarocryptands of the present invention maintain high selectivity for $K^+$ when used in aqueous media. (By highly selective is meant that the $K^+/Na^+$ complexation ratio is at least 20:1.) When the cryptand portion of the ionophore of the present invention complexes with a cation, the optical properties of the ionophore change in such a way that the concentration of cations in a particular sample can be determined by fluorometric analysis.

Coumarin substituents and their position on the coumarin ring have been chosen so as to ensure that the excitation maximum of the ionophore of the present invention falls in the general range of 350 nm to approximately 440 nm. This means that the ionophore of the present invention can be used with conventional glass optics, unlike the 4-methyl compound described in U.S. Pat. No. 5,162,525 which is reported therein to have an excitation maximum at about 330 nm. Additionally, unlike the 4-methyl compound, the substituents taught by the present invention provide a convenient and stable, both hydrolytically and thermally, means of attachment to a substrate so that the ionophores of the present invention can be easily incorporated into a continuous, blood-contacting testing method. Further, whereas the 4-methyl compound seems to undergo a drastic loss in fluorescence output when continuously irradiated at the excitation maximum (due perhaps to photooxidation of the methyl group, which is well known in related 4-methylcoumarin laser dyes), the ionophores of the present invention show good fluorescence stability.

DETAILED DESCRIPTION OF PREFERRED EMBODIMENTS

The fluorescent ionophores of the present invention have the general formula A, shown above. By placing R at the 3-position on the coumarin ring and limiting it to electron withdrawing or polarizable groups, the wavelength of the absorbance maximum of these ionophores has been raised to a point where they can be used in systems employing conventional glass optics.

The ionophores of the present invention comprise two units which together allow for the selective recognition of cation. The first of these units comprises a cryptand group. This portion of the molecule is the unit which physically interacts with the potassium ions to be analyzed. Those skilled in the art will recognize which cryptand cage will be useful in complexing a particular cation, although reference can be made to, for example, Lehn and Sauvage, "[2]-Cryptates: Stability and Selectivity of Alkali and Alkaline-Earth Macrobicyclic Complexes, *J. Am. Chem. Soc.*, 97, 6700–07 (1975). The size of the [2.2.2] cage, defined by the oxygen and nitrogen atoms (approximately 0.28 nm), makes this unit quite selective for cations with a similar diameter (e.g., $K^+$, $Pb^{+2}$, $Sr^{+2}$ and $Ba^{+2}$), whereas the size of the [2.2.1] cage (approximately 0.21 nm) makes it quite selective for cations with a similar diameter (e.g., $Na^+$ and $Ca^{+2}$), and the size of the [2.1.1] cage (approximately 0.16 nm) makes it highly selective for cations such as $Li^+$ and $Mg^{+2}$. (Advantageously, when these coumarocryptands are to be incorporated into systems which measure physiological concentrations of $K^+$, $Na^+$, or $Li^+$, the heavier metals are unlikely to be present in concentrations which can interfere the analysis of one of these ions.) This size selectivity is critical, for example, where physiological samples containing ions in addition to $K^+$ are to be quantitatively analyzed for $[K^+]$. The cryptand group can exist in mono- or diprotonated form depending on the pH of the analyte. Protonation, which occurs at the bridging nitrogens, does not significantly affect the selectivity of the coumarocryptand for $K^+$ (over other metal ions) over the physiological pH range but can affect the combined fluorescence intensity of the coumarocryptand species.

The second specialized unit of the ionophores of the present invention is a coumarin group substituted at the 3-position. This unit may be considered as the "reporting" unit. Using physiological testing as an example, the coumarin unit has a characteristic fluorescence intensity versus wavelength plot when a proton or $Na^+$ is present in the cryptand cage. When a $K^+$ forms a complex with the oxygen and nitrogen atoms of the cryptand cage, an increase in the fluorescence intensity is observed. In other words, the formation of a potassium complex increases the fluorescence quantum yield of the coumarin unit. This same mechanism holds true for other cations for which a particular cryptand group is selective.

In the present invention, the carbonyl functionality of the coumarin unit can be replaced by an imine functionality without affecting the ionophoric performance. However, if the molecules of the present invention will be used in an aqueous acidic environment, this imine functionality can hydrolyze into a carbonyl group.

The 3-position of the coumarin unit is substituted by an electron withdrawing or polarizable group, R. Unlike the examples in U.S. Pat. No. 5,162,525 (Masilimani et al.), the present invention requires that the coumarin portion of the fluorescent ionophores of the present invention be substituted at the carbon adjacent to the carbonyl/imine group. By locating R at this position, the ionophores of the present invention have somewhat greater (e.g., up to 20% greater) quantum yields than coumarins substituted at the 4-position. This means that a decreased intensity of excitation may be used, thereby reducing the likelihood of photodegradation and allowing lower intensity light sources to be used. Additionally, restricting R to only electron withdrawing or polarizable groups has been found to yield ionophores with excitation maximums which are sufficiently red-shifted (i.e., in the range of 350 to 440 nm) to allow them to be used with conventional glass optics and to further reduce susceptibility to photodegradation.

Electron withdrawing or polarizable groups that can be used as substituents in the ionophores of the present invention include carboxyl, carboxamide, sulfonylaryl, ester, keto-alkyl ester, and aromatic groups (preferably substituted at one or more positions). Preferred R groups include esters, keto-alkyl esters, and substituted aromatic groups such as substituted phenyls, benzimidazolyls, benzoxazolyls, and benzthiazolyls. Of the esters, ethyl esters are particularly preferred; of the keto-alkyl esters, —(CO)CH$_2$CH$_2$CH$_2$(CO)OCH$_2$CH$_3$ is particularly preferred. Preferred aromatic group substituents include amines, carboxylic acid, and sulfonic acid.

The carbonyl portion of the esters and keto-alkyl esters and the ring(s) of the substituted aromatic groups are far less likely to undergo photooxidation, which can occur during fluorometric analysis due to irradiation over the excitation range, than the methyl group shown in the examples of Masilimani et al. Further, where the substituent is a substituted aromatic group, a variety of substituents can provide a convenient point of covalent attachment; where the substituent is an ester or keto-alkyl ester, the carboxy portion of these groups, upon hydrolysis, similarly provides a convenient point of covalent attachment.

Preparation of the coumarocryptand ionophores of the present invention is based on a general scheme that provides a key intermediate (formula B, shown above), or its immediate precursor (III in the Reaction Scheme shown below), wherein L is a leaving group such as a halogen (other than fluorine) and alkyl- and arylsulfonates such as mesyl, tosyl, and brosyl. Various coumarins and, consequently, coumarocryptands can be synthesized from this intermediate by several methods.

In the examples, the bis-chloroethoxy species has been used although, as mentioned above, any leaving group-terminated bis-ethoxy 2-hydroxybenzaldehyde can be used. To make the bis-chloroethoxy key intermediate, 1,2-bis-(2'-hydroxyethoxy)benzene was chosen as a starting material. This starting material can be prepared according to the process described by Landini and Montanari in *Synthesis*, 223–25 (1978). This starting material is converted to 1,2-bis-(2'-chloroethoxy)benzene (I) by reaction with an excess of thionyl chloride. (See Example 1.) Compound I is then allowed to react with 1,1-dichloromethyl methyl ether in the presence of titanium chloride to produce, upon hydrolysis, 1,2-bis-(2'-chloroethoxy)benzaldehyde (II). (See Example 2.) The reaction of this compound with hydrogen peroxide and sulfuric acid yields 3,4-bis-(2'-chloroethoxy)phenol (III). (See Example 3.) Compound III is then treated with 1,1-dichloromethyl methyl ether in the presence of titanium chloride to produce, upon hydrolysis, the aforementioned key intermediate. (See Example 4.)

This intermediate can then be treated in at least two different ways in order to produce 6,7-bis-(2'-iodoethoxy)-3-carboethoxycoumarin (IV). The procedures discussed herein teach the preparation of the ester-substituted coumarocryptand, but those skilled in the art will readily see how coumarocryptands having a different R group can be made by reacting the intermediate with compounds similar to those discussed below.

First, the intermediate can be converted to 6,7-bis-(2'-chloroethoxy)-3-carboethoxycoumarin (V) by reaction with diethyl malonate in the presence of a catalyst such as piperidine or acetic acid. (See Example 5.) (Compound V can also be prepared directly from compound III by a less preferred method which is shown in Example 6.) Compound V is then treated with sodium iodide to give compound IV. (See Example 7.) Second, the intermediate can be converted to 4,5-bis-(2'-iodoethoxy)-2-hydroxybenzaldehyde (VI) by reaction with sodium iodide. (See Example 8.) Compound VI can then be condensed with diethyl malonate in the presence of a catalyst to give compound IV. (See Example 9.)

Compound IV can then be directly converted to 6,7-[2.2.2]-cryptando-3-carboethoxycoumarin by reaction with 1,4,10,13-tetraoxa-7,16-diazacyclooctadecane (i.e., 4,13-diaza-18-crown-6) and sodium carbonate. (See Example 10.)

These reactions are summarized in the Scheme shown below.

Reaction Scheme

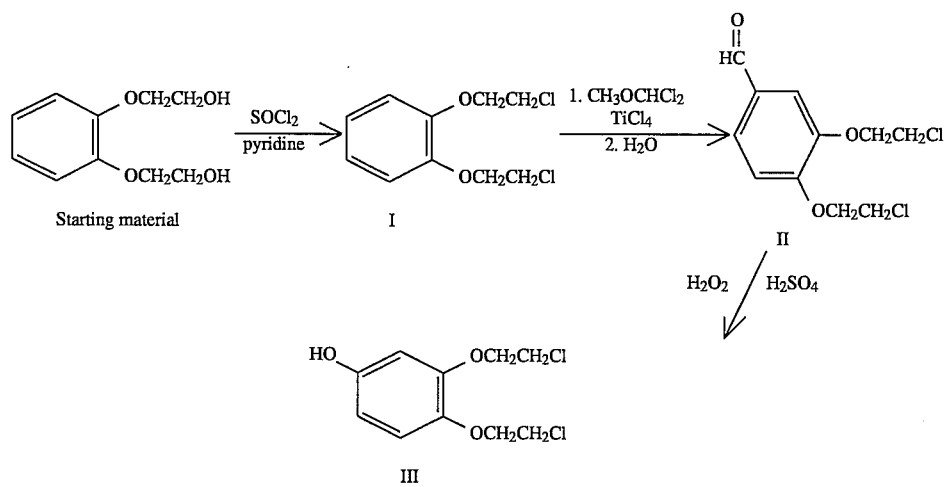

-continued
Reaction Scheme
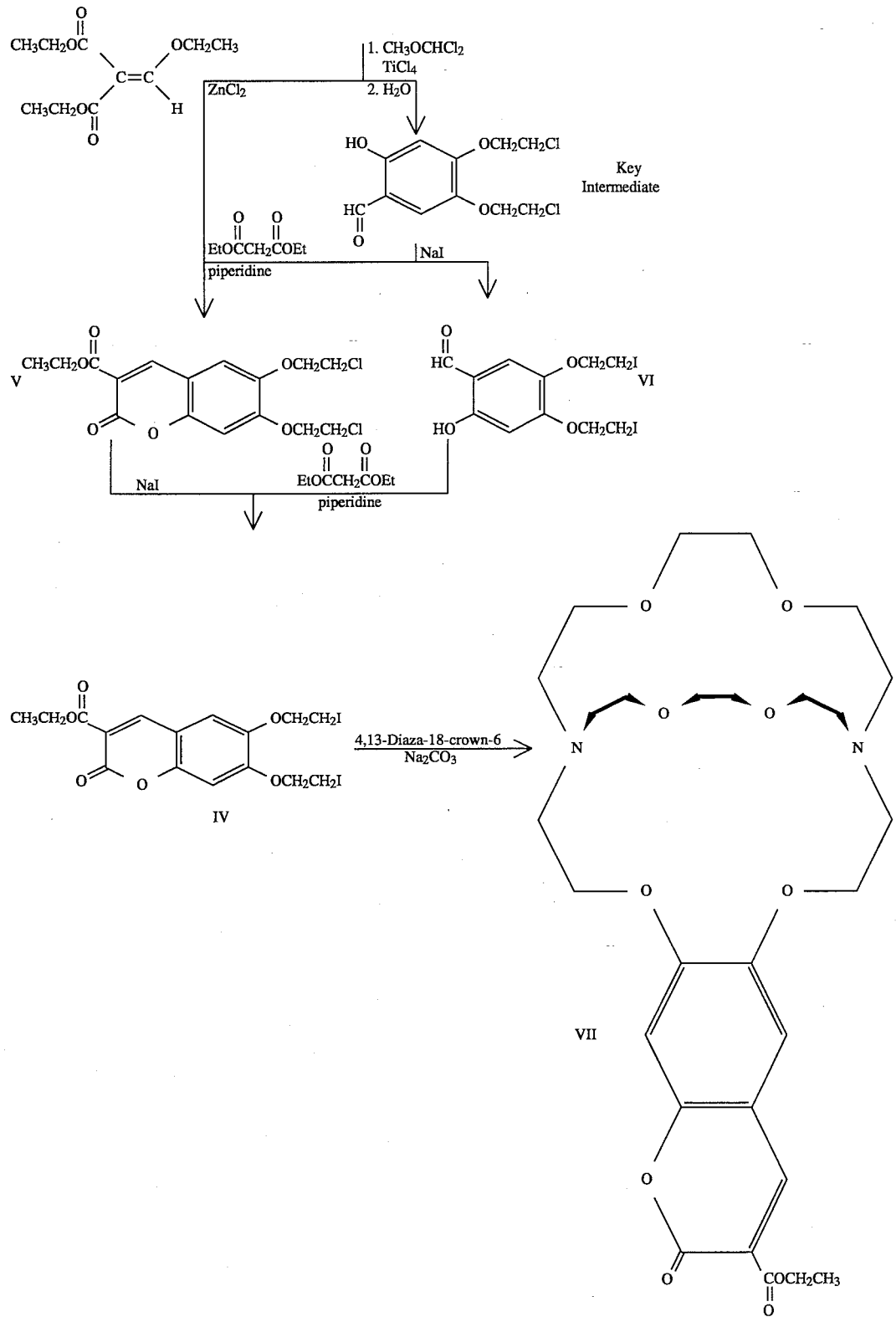
Et = ethyl

To obtain a coumarocryptand substituted with a keto-alkyl ester or a substituted aromatic group, one would need only to substitute the proper compound for diethyl malonate in the step where compound V is made from the key intermediate (or, alternatively, for diethylethoxymethylene malonate in the step where compound V is made from compound III).

Those skilled in the art will recognize that coumarocryptands other than the [2.2.2] species can be prepared by using diaza crown ethers other than 4,13-diaza-18-crown-6. For instance, where a [2.2.1] coumaro-cryptand is desired, 1,4,10-trioxa-7,13-diazacyclopen-tadecane can be used.

Potential substituents that can be attached at the 3-position on the coumarin unit provide a convenient means of covalent attachment to other molecules and/or chemical substrates. These fluorogenic ionophores can be attached to a substrate either directly or through a molecular tether (i.e., a linking group) in order to form sensing compositions, which can then be incorporated into continuous sensing or flow-through devices.

Where the ionophores of the present invention are attached to a substrate through such linking groups, the longest continuous chain thereof preferably comprises 5 to 125 carbon and/or hetero atoms such as oxygen, nitrogen, etc., more preferably 10 to 70 carbon and/or hetero atoms, with a free functionality on at least one end thereof. These linking groups are preferably hydrophilic so as to not interfere with the capacity of metal ions to interact with the ionophores. However, if it is desired that the linking groups contribute to a different physical property of the system (e.g., hydrophobicity, negative charge, etc.) or if the substrate is sufficiently hydrophilic, the repeating units and end group functionalities can be chosen accordingly.

The functionalities of these linking groups can be chosen so as to selectively react with the R group of the coumarocryptand. Possible functional groups include amines, amides, esters, oxiranes, olefins, ureas, isocyanates, thioisocyanates, carbamates, sulfonamides, sufonyl chlorides, carboxyls, silanols, chlorotriazines, hydrazines, hydrazides, and aldehydes (or groups which, upon reaction with the R group of the coumarocryptand, form amines, amides, esters, ethers, ureas, urethanes, sulfonamides, silanes, and hydrazides).

The linking groups are preferably attached to the substrate before reaction with the ionophores. This can be done in one of two ways. First, they can be reacted with the substrate before attaching the ionophores. If this option is chosen, each linking group must be bireactive (i.e., have a functional group, either the same or different, on each end of each tether), and the substrate must have complementary functionalities which will react with one of the functional groups of the tethers. Second, the substrate can be formed with linking groups preattached. This involves choosing the substrate polymer so that linking groups are already appended.

Where the ionophores of the present invention are to be immobilized on a substrate (i.e., either directly or through a linking group) to form a sensing composite structure, substrates of various forms can be employed. Where the sensing composite is to be included in a continuous monitoring device, a planar substrate will probably be preferred, simply because of the dimensions and geometry of the device.

Examples of planar substrates or substrates that can readily be made planar include (free-standing) polymeric membranes and coatable polymers (i.e., polymers that can be coated on a support). Membranes can be formed from various polymers including polyethylene, polypropylene, polyvinylidene chloride, polyvinylchloride (PVC), polysulfone, nylon, and silica. (Some nylon membranes provide poorly reversible composites, i.e., composites that can be used for only a few cycles between high and low cation concentration before slowly ceasing to show changes in intensity with changing metal ion concentration.) These membranes are preferably ion permeable and are optionally functionalized with, or have been treated (e.g., air oxidation) so as to intrinsically carry, groups that are complementary to and react with the functionality of R (from the ionophore).

In order to achieve as high a concentration of ionophores as possible where they are to be attached to the surface of a membrane, it may be desirable to roughen the surface of the membrane, such as one comprising silica, prior to attaching the ionophores or to use a porous membrane.

Water-insoluble coatable polymers are a preferred substrate. Such polymers include PVC, copolymers and terpolymers of PVC, copolymers of styrene and maleic acid or maleic anhydride, copolymers of alkyl vinyl ether and maleic acid or maleic anhydride, polymers and copolymers of vinyldimethyl azlactone, and copolymers of acrylate- and methacrylate esters (or acrylamides and methacrylamides) with acrylic acid and methacrylic acid. Once the ionophores of the present invention have been covalently attached to one of these polymers (either directly or through linking groups), the polymer-ionophore composite optionally can be spread on one of the membranes described above. Alternatively, a membrane can be coated with a coatable polymer (optionally reacted with linking groups) and then allowed to react in a solution of an ionophore of the present invention. When either is done, the substrate is the membrane plus the coatable polymer bearing the ionophore.

An additional advantage provided by the use of a PVC polymer or copolymer is that the pH dependence of the fluorescence response of the coumarocryptand is reduced. For example, the change in fluorescence intensity of such a sensing composite structure at physiological pH (7.3 to 7.5) and physiological $K^+$ concentration (about 4 mM) is only about 2% of the total fluorescence intensity change.

A particularly preferred composite structure is a preformed membrane coated with PVC which has been reacted with (either directly or through a tether) a 3-coumarocryptand of the present invention. Of available preformed polymeric membranes, a particularly preferred one is hydrophilic porous polypropylene (HPPP), described in PCT patent publication WO 92/07899, because it allows unhindered access to the ionophore by metal ions without showing strong affinity for them. This type of composite structure optionally can be formed into a rolled plug.

Those skilled in the art will recognize that, by merely selecting a membrane that is selectively permeable for protons (or the hydronium ion), a composite structure that acts as a pH sensor in the presence of varying concentrations of metal ions can be prepared. Where a constant concentration of metal ions is maintained, such a selective membrane might not be needed.

Where a flow-through device is to be employed, a solid composite structure can, for example, be ground into a powder (or the coumarocryptand compound can be attached to commercially available powders or beads) or encapsulated in an ion permeable matrix such as a hydrogel, an acrylamide or an acrylate-type gel. If the composite structure a powder (or is ground into a powder), it can be adhered to a planar substrate if so desired.

Where continuous sensing is desired, the substrate, notwithstanding the particular geometry employed, will preferably either not interact with or will allow for reversible interaction with cations in its vicinity (so that the ions can easily form reversible complexes with the attached ionophores). To minimize interference with the cation/ionophore equilibrium, the substrate material chosen preferably interacts with cations in such a way that the reversibility of this interaction is not significantly modified when the concentration of cations changes. The substrate itself preferably will not be irreversibly reactive with or adsorb cations, will have a net negative charge, and will be hydrophilic. If the substrate chosen does not intrinsically possess these preferred characteristics, it can be modified so that it does. For instance, sulfonate or phosphate groups can be attached along with the aforementioned linking groups in order to impart to the composition an overall negative charge and to increase its hydrophilicity.

Where the sensing composition is to be used in a device where cations must diffuse through the substrate in order to reach the attached ionphores, the substrate will necessarily be at least somewhat ion permeable or microporous. Additionally, depending on whether (and how) an interrogation beam of light is to be used, it may be desirable to provide a translucent or transparent substrate and an opaque, reflecting, or light absorbing overcoat. Typical overcoats include a polymeric dispersion of carbon black (coated on the substrate) and ink.

If the concentration of cations in the analyte solution is to be quantitatively determined, an analytical technique that can measure the equilibrium ion - ionphore complex concentration is preferred. Spectroscopic methods have been found to be especially useful. Particularly preferred is fluorescence. Such a method optionally can be modified so as to employ fiber optics in the transmission of excitation and emitted light. For instance, one or more optical fibers can be used to introduce interrogating light of a wavelength range centered around $\lambda_1$, and to transport to a detector emitted light of a wavelength range centered around $\lambda_2$.

The fluorescent ionphoric compounds of the present invention can be used in a variety of applications wherein the determination of the concentration of a particular cation is desired. ionphores selective for $K^+$ or $Na^+$ are particularly useful in the determination of the concentrations of these ions, especially in biological systems. These ionphores can be incorporated into existing testing kits, coated onto various substrates, and incorporated in fiber optic-based analytical instruments. Ionphores selective for $Pb^{+2}$ can be useful in environmental and perhaps even biological testing. By confining coumarocryptand ionphores that have a $pK_a$, preferably a $pK_a$ for the diprotonated species, near the pH of interest in a suitably buffered water-filled compartment inside (or, perhaps, behind) a silicone rubber or similarly gas-permeable membrane, one can also determine $[CO_2]$ (i.e., the ionphore can interact with the acidic species generated by the hydration of $CO_2$ to $H_2CO_3$). Other detection and concentration determination applications using these ionphores will be apparent to those skilled in the art.

Objects and advantages of this invention are further illustrated by the following examples. The particular materials and amounts thereof, as well as other conditions and details, recited in these examples should not be construed to unduly limit this invention.

EXAMPLES

Examples 1 to 10 describe various steps in the preparation of 6,7-[2.2.2]-cryptando-3-carboethoxycoumarin (VII). Example 11 describes hydrolysis of the ester moiety of this compound.

Example 1

1,2-bis-(2'-chloroethoxy)benzene

A solution of 6 g (0.03 mol) of 1,2-bis-(2'-hydroxyethoxy)benzene (prepared according to the procedure of Landini and Montanari) in 400 ml of toluene and 6 ml of pyridine was heated under nitrogen to 40° C. Excess thionyl chloride (9.2 ml, 0.13 mol) was added, with stirring, over a period of 25 minutes. The reaction mixture was heated to the boiling point (about 110° C.) and maintained at reflux for 3 hours. The solution was cooled to room temperature before being decanted and saved. The residue was broken up, dissolved in water, and extracted with toluene. The toluene solutions were combined and washed first with 2N HCl, then with a saturated sodium bicarbonate solution. The dried solution was evaporated in vacuo to give 4.5 g (64%) of crude product which was distilled by kugelrohr at aspirator pressure to give 4.43 g of an analytically pure sample, m.p. 55°–56.5° C. Spectroscopic analysis confirmed that the product was 1,2-bis-(2'-chloroethoxy)benzene.

Example 2

1,2-bis-(2'-chloroethoxy)benzaldehyde

This procedure is a modification of a method used in the synthesis of mesitaldehyde as described in *Org. Synth. Coll.*, vol. V, 49–51 (1973) and *Chem. Ber.*, 96, 308–13 (1963).

A solution of 25 g (0.11 mol) of the product of Example 1 in 60 ml of methylene chloride was cooled to 0° C. A total of 20 ml (0.18 mol) of titanium tetrachloride (Aldrich Chem. Corp.; Milwaukee, Wis.) was added by syringe over 30 minutes, under nitrogen, with stirring while the solution was maintained at the 0° C. reaction temperature. A solution of 13.5 g (0.117 mol) of 1,1-dichloromethyl methyl ether (Aldrich) in 10 ml of methylene chloride was added over 15 minutes at 0° C. Stirring at 0° C. was continued for 5 minutes. The solution was warmed for 20 minutes on a water bath until the solution reached room temperature. It was then refluxed for 15 minutes. After the solution had cooled, it was poured over crushed ice. After shaking the mixture in a separatory funnel, the methylene chloride layer was separated, and the aqueous layer was extracted with two 100 ml portions of chloroform. The chlorocarbon solutions were combined and washed extensively with first water, then a brine solution. The organic layer was dried and evaporated in vacuo to give 24.5 g of the aldehyde (87%) as an acrid, saffron-yellow solid with a m.p. 49°–51° C. Spectroscopic analysis confirmed that the product was 1,2-bis-(2'-chloroethoxy)benzaldehyde.

Example 3

3,4-bis-(2'-chloroethoxy)phenol

This compound was initially prepared by Baeyer-Villiger oxidation of the benzaldehyde from Example 2 to the formate ester using 3-chloroperoxybenozoic acid or magnesium monoperoxyphthalate, followed by acid-catalyzed hydrolysis. However, upon scale up, this method led to catastrophic loss of product through decomposition. Therefore, an alternative to the Baeyer-Villiger method was used.

In a two-liter flask equipped with an overhead stirrer and a cooling bath was placed 162 g (0.616 mol) of the product of Example 2 and 1.5 liters of chilled (10° C.) methanol. To this solution was added 48 g of a 33% (by wt.) sulfuric acid solution which had been pre-cooled.

To 125 ml of methanol was added 94 g (0.83 mol) of a 30% (by wt.) hydrogen peroxide solution and this mixture was added over five minutes, with stirring and continued cooling, to the above solution. The resultant solution became turbid but, after two hours of stirring, it clarified.

The solution was decanted away from a brown oil (11 g, discarded) that had formed on the bottom of the reaction flask. The decanted solution was stirred overnight at room temperature. Methanol was stripped from the reaction mixture before 400 ml chloroform and 100 ml water were added to the crude product. This mixture was agitated.

After the layers separated, the aqueous layer was further extracted with chloroform. The chloroform layers were combined and washed with water to a neutral pH. The organic layer was then extracted with a solution of 30 g (0.75 mol) NaOH in 400 ml water followed by a second 200 ml portion of a similarly prepared NaOH solution. The aqueous extracts were combined, acidified with 200 ml 6N HCl, and extracted with 400 ml fresh chloroform. The chloroform layer was dried over sodium sulfate and passed through a 5 cm×5 cm plug of silica. On removal of the solvent, 84 g (54%) of a slightly brown solid was obtained. Proton NMR confirmed the structure of the product.

Example 4

4,5-bis-(2'-chloroethoxy)-2-hydroxybenzaldehyde

This key intermediate was prepared by the method which was used to introduce the aldehyde functionality to 1,2-bis-(2'-chloroethoxy)benzene in Example 2.

In 60 ml of methylene chloride, 12.4 g (49.4 mmol) of the crude phenol from Example 3 was treated with 16.3 ml (148 mmol) of titanium tetrachloride followed by 4.5 ml (50 mmol) of 1,1-dichloromethyl methyl ether to give 5.2 g (37%) of the key intermediate. This product was sublimed at oil pump vacuum to give 4.35 g of cream-white crystals having a m.p. of 102°14 102.5° C. Spectroscopic analysis confirmed that the product was the key intermediate.

Example 5

6,7-bis-(2'-chloroethoxy)-3-carboethoxycoumarin (First method)

This method is a standard Knoevenagel condensation on the 2-hydroxybenzaldehyde of Example 4 and is based on the methods of Balaiah et al., *Proc. Indian Acad. Sci.*, 16A, 68–82 (1942) (*Chem. Abs.*, 37, 1429 (1943)); Borsche et al., *Chem. Ber.*, 85, 198–202 (1952 ); Fukui et al., *Bull. Chem. Soc.* Japan, 35, 1321–23 (1962).

To 6.03 g (37.6 mmol) diethyl malonate (Aldrich) was added and thoroughly mixed 10 g (36 mmol) of the product of Example 4. This mixture was heated, under nitrogen, on a steam bath. After dissolution, two drops of piperidine were added. Heating was continued for 30 minutes. The solution was then cooled and diluted with ethanol until a slurry resulted. After filtration and air drying, 11.5 g (85%) of a tan powder were obtained. It had a m.p. of 102°–103.5° C. The Proton NMR spectrum was identical to that obtained for the product of Example 6.

Example 6

6,7-bis-(2'-chloroethoxy)-3-carboethoxycoumarin (Second method)

This method, based on Bissel, *Synthesis*, 846–48 (1982), proved to be erratic and, when successful, gave a low yield. Its one advantage is that it provides Compound V directly from the phenol of Example 3, thus resulting in one less step.

A 0.9 g (4 mmol) portion of the phenol from Example 3 was mixed with 0.9 ml (5 mmol) diethyl ethoxymethylene malonate (Aldrich). To this solution was added 5 ml of a 1M $ZnCl_2$ solution in ether (Aldrich) along with 40 ml methylene chloride. The solution was refluxed for 24 hours under nitrogen, freed of solvent by distillation under vacuum on a rotary evaporator at aspirator pressure, and quenched with water. This mixture was extracted with chloroform. Chromatography on a short column of alumina, using methylene chloride as the eluting solvent, gave 0.33 g (24%) of the product. Proton NMR showed that the product was 6,7-bis-(2'-chloroethoxy)-3-carboethoxycoumarin.

Example 7

6,7-bis-(2'-iodoethoxy)-3-carboethoxycoumarin (First method)

This follows the procedure described in Example 3 of U.S. Pat. No. 5,162,525 for the corresponding 4-methyl derivative.

A 0.75 g (2.0 mmol) portion of the bis-chloroethoxycoumarin from Example 5 and 0.9 g (6 mmol) of sodium iodide were dissolved in 25 ml acetone. The solution was refluxed under nitrogen for 2 days. Thereafter, an additional 0.45 g sodium iodide was added. The solution was refluxed for another 24 hours. (It was later discovered that using methyl ethyl ketone in place of acetone shortens the total reaction time to approximately 24 hours.) A final 0.45 g of sodium iodide was added. Reflux was maintained for an additional 6 days. Acetone was added as needed to maintain the original reaction volume. The solution was cooled and evaporated in vacuo. The residue was extracted with a mixture of methylene chloride and chloroform. The chlorocarbon solution containing the product was washed with 10% sodium thiosulfate (to reduce to iodide any iodine that had formed), dried over sodium sulfate, and evaporated to dryness on a rotary evaporator. The residue was crystallized from ethanol to give 0.92 g (82%) of a light yellow powder having a m.p. of 164°–166° C. The proton NMR spectrum of the product was in agreement with that of the product of Example 9.

Example 8

4,5-bis-(2'-iodoethoxy)-2-hydroxybenzaldehyde

This Example provides one of two alternate routes to the bis-iodoethoxycoumarin derivative in Example 9 (IV).

In 20 ml acetone were dissolved 2.21 g (14.7 mmol) sodium iodide and 1.37 g (4.91 mmol) of the product of Example 4. The solution was refluxed for four days. Thereafter, 10 ml acetone and a second portion of sodium iodide (0.73 g, 2.6 mmol) were added, and the solution was refluxed another 24 hours. The solution was cooled and filtered. Solvent was removed on a rotary evaporator, and the residue was dissolved in chloroform. After the chloroform solution was washed with water and dried with sodium sulfate, solvent was removed to give 2.05 g (89%) of product. Proton NMR confirmed the structure of the product.

Example 9

6,7-bis-(2'-iodoethoxy)-3-carboethoxycoumarin (Second method)

To 1.73 g (10.8 mmol) of the bis-iodoethoxyhydroxybenzaldehyde from Example 8 was added diethyl malonate, 2.1 g (4.6 mmol), and this mixture was heated on a steam bath. When the mixture had become homogeneous, two drops of piperidine were added. After the mixture had cooled, a precipitate formed. The solution was diluted with a few milliliters of ethanol and reheated to boiling on the steam bath. After the solution had cooled, it was filtered and the precipitate product retained. The product was a solid with a m.p. of 162°–165° C. Proton NMR confirmed the structure of the product.

Example 10

6,7-[2.2.2]-cryptando-3-carboethoxycoumarin

The method described in Example 4 of U.S. Pat. No. 5,162,525 for the corresponding 4-methyl derivative was used to prepare this coumarocryptand.

A 1.0 g (1.8 mmol) sample of bis-iodoethoxycoumarin (from Example 7 or Example 9) and 0.47 g (1.8 mmol) of 1,4,10,13-tetraoxa-7,16-diazacyclooctadecane (i.e., 4,13-diaza-18-crown-6) were separately dissolved in 50 ml portions of dry acetonitrile. The combined solutions (100 ml total) were refluxed under nitrogen for six days in the presence of 5 equivalents (0.94 g) anhydrous sodium carbonate. During the reaction, the coarse sodium carbonate was converted to an extremely fine powder. The cooled reaction mixture was filtered and the solution was evaporated to dryness in vacuo. The residue was dissolved in methylene chloride, and the solution was filtered. Evaporation of the methylene chloride using the rotary evaporator at aspirator pressure, followed by oil pump pressure, gave a yellow foam (>100% of the calculated yield). The crude product was purified by chromatography on deactivated neutral alumina first using methylene chloride to elute unreacted starting materials, followed by a 1–5% ethanol/methylene chloride mixture to elute the product. About 50% of calculated amount of the product was recovered, consisting essentially of the desired product (VII). LRMS FAB (triethanolamine) calculated m/e for $C_{28}H_{40}N_2O_{10}$ was 564.27, whereas the observed m/e was 587, $[VII \subset (Na)]^+$; free $[VII]^+$ was not observed. UV (phosphate buffered saline) $\lambda_{max}$=374 nm, 312 nm. Fluorescence (phosphate buffered saline) showed $\lambda_{ex}$=371 nm and $\lambda_{em}$=453 nm.

The structure of a similarly prepared sample that was further purified by additional chromatography was confirmed by proton NMR.

Example 11

Hydrolysis of coumarocryptand of Example 10

A 0.25 g sample of the product of Example 10 was dissolved in 25 ml 2N HCl and heated on a steam bath for 30 minutes. Small amounts of methanol were added as needed to promote dissolution. Volatile components of the reaction (i.e., water, excess HCl, alcohols) were evaporated first on the rotary evaporator at aspirator vacuum, then quiescently at oil pump vacuum, to give the 3-carboxy-cryptandocoumarin hydrochloride salt, a pumpkin-yellow solid. Proton NMR confirmed the desired product.

Examples 12–14 describe the preparation of another coumarocryptand.

Example 12

6,7-bis-(2'-chloroethoxy)-3 -(1'-oxo-4'-carboethoxybutyl)coumarin

Using the method described in Example 5, a solution of 2.12 g (7.60 mmol) of the product of Example 4 and 1.76 g (7.64 mmol) of diethyl 3-oxo-pimelate (Aldrich) in 100 ml ethanol was heated on a steam bath. About 20 drops of piperidine were added. The mixture was refluxed for thirty minutes and cooled to room temperature. The precipitate that formed was isolated by filtration and dried to yield 3.53 g (96%) of product. The structure of the product was confirmed by proton NMR.

Example 13

6,7-bis-(2'-iodoethoxy)-3 -(1'-oxo-4'-carboethoxybutyl)coumarin

Using the method described in Example 7, a solution of 3.5 g (7.5 mmol) of the product of Example 12 and 3.4 g (23 mmol) anhydrous sodium iodide in 300 ml methyl ethyl ketone was heated to reflux under nitrogen for 48 hours. The mixture was cooled to room temperature, and the solvent was removed by rotary evaporation in vacuo. The residue was treated with about 20 ml water. The solid that remained was isolated by filtration and dissolved in toluene. The toluene was removed by rotary evaporator at reduced pressure to scavenge any residual water. The product was dried under high vacuum to afford 4.5 g (95%) of the desired product. Proton NMR was used to confirm the structure of the product.

Example 14

6,7-[2.2.2]-cryptando-3 -(1'-oxo-4'-carboethoxybutyl)coumarin

The method described in Example 10 was adapted as follows: In a 250 ml flask equipped with a magnetic stirrer, reflux condenser, and a nitrogen purge source was placed 0.79 g (1.3 mmol) of the product of Example 13 dissolved in dry acetonitrile (45 ml, dried over silica gel and 0.4 nm molecular sieves, and distilled from calcium hydride). One equivalent (0.33 g) of 4,13-diaza-18-crown-6 was dissolved in a second portion (20 ml) of dry acetonitrile, and this solution was added to the first solution. The reaction mixture was heated to 70° C. before 0.62 g (5.8 mmol) sodium carbonate was added. The solution was refluxed under nitrogen for 7 days. Thereafter, 60 ml chloroform was added, and the solution was filtered.

After solvent was stripped, approximately 1 g of a yellow tacky oil was obtained. To the oil were added 60 ml chloroform and 20 ml brine, and this combination was mixed. The organic layer was separated and dried over sodium sulfate. Stripping the solvent gave 0.85 g of oily product. This was purified first by flash chromatography through a 2 cm×6 cm column of aluminum oxide powder (using 70 ml methylene chloride as the eluting solvent) to leave 0.65 g of product. This material was then carefully passed through a second column of aluminum oxide using a 1:2 mixture of methylene chloride/hexanes to give 370 mg (46%) of essentially pure product, a sticky yellow powder.

Proton NMR and IR spectroscopy was used to confirm the structure of the product. UV spectroscopy (phosphate-buffered saline) results: $\lambda_{max}$=382 nm, 317 nm.

Example 15

Comparison of Photostabilities of Coumarin Derivatives

The following model compounds were used to assess the effect on relative photostability of changes in functionality at the 3- and 4-position in coumarins.

Solutions of compounds VIII, IX, X, and XI in ethanol were prepared with absorbances in the range $0.05 \leq A_{max} 23$ 0.1, and each was continuously irradiated in a SPEX Fluorolog 2™ Series spectrofluorimeter (SPEX Industries, Inc.; Edison, N.J.) at maximum source slit widths (30 nm band pass) at $\lambda_{max}$ for an hour. Measured luminance of the excitation source at the sample ranged from 30 to 50 mW/cm². The intensity of fluorescence was monitored throughout the duration of the irradiations at the emission maximum for each.

The data, normalized to X, are shown below in Table I. (The photostability of compounds VIII, IX, and X were measured in one experiment and that of compound XI in another, but the results are combined into a single Table for ease of comparison.)

The difference in the intensities at time zero reflects the relative fluorescence efficiencies of the derivatives. The 3-carboethoxy derivative (VIII) combines superior photostability with a slightly improved fluorescence efficiency over the 4-methyl derivative (IX) or carboxymethyl derivative (XI).

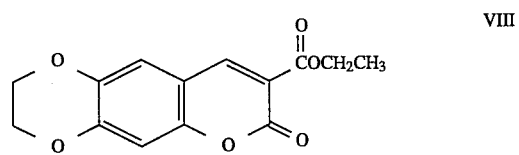

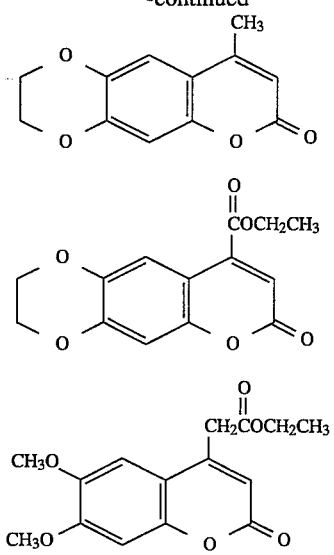

TABLE I

| Time (sec) | Intensity of Coumarins VIII–XI | | | |
|---|---|---|---|---|
| | VIII | IX | X | XI |
| 0 | 6.94 | 6.15 | 1.00 | 8.97 |
| 120 | 6.95 | 5.99 | 1.00 | 8.90 |
| 240 | 6.94 | 5.82 | 1.00 | 8.74 |
| 360 | 6.93 | 5.78 | 1.00 | 8.60 |
| 480 | 6.93 | 5.68 | 1.00 | 8.47 |
| 600 | 6.91 | 5.57 | 1.00 | 8.34 |
| 720 | 6.91 | 5.52 | 1.00 | 8.22 |
| 840 | 6.90 | 5.45 | 1.00 | 8.10 |
| 960 | 6.90 | 5.39 | 1.00 | 7.98 |
| 1080 | 6.89 | 5.28 | 1.00 | 7.86 |
| 1200 | 6.88 | 5.21 | 1.00 | 7.76 |
| 1320 | 6.87 | 5.12 | 1.00 | 7.62 |
| 1440 | 6.87 | 5.04 | 1.00 | 7.52 |
| 1560 | 6.86 | 4.97 | 1.00 | 7.42 |
| 1680 | 6.85 | 4.89 | 1.00 | 7.31 |
| 1800 | 6.84 | 4.81 | 1.00 | 7.19 |
| 1920 | 6.84 | 4.74 | 1.00 | 7.09 |
| 2040 | 6.83 | 4.65 | 1.00 | 6.99 |
| 2160 | 6.82 | 4.55 | 1.00 | 6.89 |
| 2280 | 6.81 | 4.46 | 0.99 | 6.79 |
| 2400 | 6.81 | 4.37 | 0.99 | 6.68 |
| 2520 | 6.80 | 4.27 | 0.99 | 6.59 |
| 2640 | 6.79 | 4.22 | 1.00 | 6.50 |
| 2760 | 6.78 | 4.12 | 0.99 | 6.39 |
| 2880 | 6.77 | 4.05 | 0.99 | 6.29 |
| 3000 | 6.77 | 3.98 | 1.00 | 6.20 |
| 3120 | 6.76 | 3.92 | 0.99 | 6.11 |
| 3240 | 6.75 | 3.85 | 0.99 | 6.01 |
| 3360 | 6.74 | 3.76 | 0.99 | 5.92 |
| 3480 | 6.73 | 3.70 | 0.99 | 5.83 |
| 3600 | 6.72 | 3.64 | 0.99 | 5.74 |

Example 16

Response of Coumarocryptand of Example 10 to Changes in [K$^+$] at Physiological Concentrations An approximately 10$^{-5}$M solution of the product of Example 10 ($A_{372nm}$=0.1) was prepared with sodium-only phosphate-buffered saline (20° C., pH=7.36, [Na$^+$]=134 mM, [K$^+$]=0 mM, [Cl$^-$]=64 mM). Aliquots (36 μl) of phosphate-buffered saline having [K$^+$]=0.2M were added to 3 ml of solution in a cuvette to change [K$^+$] in 2.4 mM steps from 0 to 12 mM. At each step, the fluorescence emission intensity was measured from 400 to 600 nm at an excitation wavelength of 270 nm.

The data were normalized to the intensity at [K$^+$]=0 mM and λ=445 nm. The normalized data, shown in Table II, demonstrate the regular increase in fluorescence intensity with increasing [K$^+$]. Increasing the [Na$^+$] to 145 mM changed the fluorescence only slightly. Similar results were obtained for the product of Example 14.

TABLE II

| λ | Intensity with Increasing [K$^+$] | | | |
|---|---|---|---|---|
| | 0 mM | 2.4 mM | 4.8 mM | 9.6 mM |
| 400 | 0.059 | 0.061 | 0.060 | 0.060 |
| 410 | 0.227 | 0.229 | 0.238 | 0.238 |
| 425 | 0.659 | 0.692 | 0.707 | 0.725 |
| 430 | 0.779 | 0.826 | 0.861 | 0.892 |
| 445 | 1.000 | 1.086 | 1.135 | 1.177 |
| 450 | 0.996 | 1.088 | 1.144 | 1.196 |
| 460 | 0.966 | 1.057 | 1.102 | 1.186 |
| 470 | 0.839 | 0.918 | 0.971 | 1.033 |
| 480 | 0.701 | 0.778 | 0.809 | 0.859 |
| 490 | 0.552 | 0.616 | 0.648 | 0.684 |
| 500 | 0.423 | 0.472 | 0.506 | 0.531 |
| 510 | 0.331 | 0.363 | 0.392 | 0.411 |
| 520 | 0.248 | 0.273 | 0.293 | 0.305 |
| 530 | 0.183 | 0.200 | 0.220 | 0.230 |
| 540 | 0.138 | 0.152 | 0.155 | 0.166 |
| 550 | 0.096 | 0.110 | 0.121 | 0.129 |
| 560 | 0.070 | 0.080 | 0.087 | 0.090 |
| 570 | 0.054 | 0.058 | 0.063 | 0.065 |
| 580 | 0.038 | 0.044 | 0.048 | 0.050 |
| 590 | 0.028 | 0.030 | 0.037 | 0.037 |
| 600 | 0.021 | 0.024 | 0.028 | 0.027 |

Example 17

Functionalization of a Coatable Polymer with Molecular Tethers

In one liter of tetrahydrofuran (THF) at room temperature was dissolved 20 g poly(vinylchloride)-carboxylated (PVC-COOH) polymer, 1.8% COOH, (Aldrich). To this was rapidly added 75 ml of a solution of 4.9 g (3 equivalents) dicyclohexylcarbodiimide (DCC) (Aldrich) in THF. After the mixture was stirred in a capped flask at room temperature for 30 to 60 minutes, 72 g (10 equivalents) Jeffamine ED-900™ bis(2-aminopropyl)polyethylene glycol 800 (available from Fluka Chemical Corp.; Ronkonkoma, N.Y.) was rapidly added to the activated polymer solution to provide a cloudy solution/suspension. This was stirred, at room temperature, for 18 hours. The solution was concentrated to approximately 300 ml on a rotary evaporator (60° C.) and slowly added to a rapidly stirred container of water (approximately 18 liters). (A low shear movement, i.e., swirling, of the water is necessary to avoid small particulates and to provide a polymer precipitate that can be readily filtered and purified.)

The polymer was removed from the water and filtered using a plastic mesh sheet, then suspended in about 500 ml methanol and again filtered. The polymer was suspended in methanol and filtered two additional times to reduce the residual water and remove reaction byproducts before being dried under vacuum.

The polymer was redissolved in about one liter THF at room temperature and filtered, first through a polypropylene filter cloth and then through a polyethylene Buchner funnel (350–600 ml) containing a thick (3 to 4 cm) pad of Celite™ 545 (Fisher Scientific; Pittsburgh, Pa.) diatomaceous earth on a poly(propylene) filter cloth. The clear filtrate was collected and concentrated to 200 ml on a rotary evaporator at 60° C.

Reprecipitation of the polymer solution in water and filtration of the polymer was conducted as described above. Fine chopping of the polymer in water (using a blender) was performed as a final step prior to vacuum drying.

An infrared spectrum of the functionalized polymer film was acquired to confirm the reaction (i.e., the disappearance of the 1720 cm$^{-1}$ absorbance characteristic of the COOH group). Gel permeation chromatography of the polymer showed that the molecular weight was essentially unchanged from that of the PVC-COOH starting material (i.e., 160,000 to 220,000 depending on the PVC-COOH lot).

The procedure of Sarin et al., *Anal. Biochem.*, 117, 147 (1981) was adapted as follows to determine the concentration of available primary amine (from the bis(2-aminopropyl)poly(ethylene glycol)). To a 20 mg sample of dry polymer in a test tube was added (a) 0.40 ml of a solution of phenol and KCN in pyridine and (b) 0.10 ml of a solution of ninhydrin in ethanol (both of which were prepared as described in the reference). A test blank was similarly prepared. Both test tubes were heated at 100° C. for approximately ten minutes. Both were cooled in a cold water bath before 2 ml tetrahydrofuran (THF) was added to each. After the contents of the tubes were transferred to separate 25 ml volumetric flasks, they were diluted to 25 ml with THF. UV spectroscopy ($\lambda_{abs}$=604 nm), with an extinction coefficient of $1.2 \times 10^4 M^{-1} cm^{-1}$, was used to determine ninhydrin concentration. From this, the concentration of available amine was determined to be 0.2 mmol/g of polymer.

Example 18

Attachment of Compound VII to Coatable Polymer

A 200 mg sample of the PVC/bis(2-aminopropyl)-poly(ethylene glycol) from Example 17 was dissolved in 10 ml dimethylformamide (DMF). A second solution of 50 mg (approximately 90 µmol) of hydrolyzed VII in 2 ml DMF was also prepared. To the second solution were added 42 µl (0.27 mmol) diisopropylcarbodiimide (Aldrich) and 40 mg (0.27 mmol) hydroxybenzylthiazole (Aldrich), and this mixture was stirred for about 20 minutes before being added to the first solution. (The flask holding the second solution was washed with 1 ml DMF to ensure complete transfer.)

To the combined mixture was added 50 µl (0.27 mmol) diisopropylethylamine (Aldrich). This was allowed to stir, under nitrogen atmosphere and in darkness, overnight.

The volume of solvent was reduced by rotary evaporation at 40° C. The concentrated solution was added slowly, with stirring, to 200 ml water. A flocculent precipitate was collected by pouring the aqueous suspension over an 80-mesh screen. The precipitate was washed four times with water and three times with methanol. After the precipitate was chopped into finer pieces with a razor blade, it was washed three more times in methanol. The functionalized polymer was dried in vacuo.

The method of Kaiser et al., Anal. Biochem., 34, 595 (1970) using ninhydrin as reagent indicated greater than 95% of the amine groups of the tethered bis(2-aminopropyl)poly(ethylene glycol) had been consumed, presumably via coupling with VII.

Example 19

Coating of Functionalized Polymer on a Porous Membrane

A 2% (w/w) solution of the functionalized polymer from Example 18 in a 90/10 (v/v) mixture of THF and water was extrusion coated onto a roll (27.9 cm wide, 79 µm thick) of hydrophilic porous polypropylene (see WO 92/07899) using a six inch-wide slot-fed knife die. (The HPPP web had a maximum pore size of 1.3 µm and a porosity of 77%.) The web speed was 3 m/min, and the solution delivery rate was 67 ml/min.

The coated web was passed through an air floatation oven (15.6° C.) to evaporate solvent. The resultant dry coating weight was about 2.5 g/m$^2$.

Exposure to 0 and 8 mM K$^+$ solutions and calculation of the percent response suggested that an asymmetric functionalized polymer coating had been distributed throughout the internal pore surface area of the HPPP web with a predominance of material added to the side of the membrane that contacted the die.

Example 20

Testing of Coated Membrane

Circular disks were punched from the coated HPPP membrane of Example 19. These were used to test the reversibility, pH-dependence, and stability (both in buffer and in blood) of the sensing composite.

Reversibility

The reversibility of the sensor to changes in potassium ion concentration was determined by measuring sensor fluorescence intensity using a CDI™ S400 monitor (CDI/3M Health Care; Tustin, Calif.) which provided an excitation source at 395 nm and detected fluorescence at wavelengths greater than 440 nm. Potassium ion concentration was varied by rapidly circulating a 50 mM N-(2-hydroxyethyl)piperazine-N'-(ethanesulfonic acid) buffer (Sigma Chemical Corp.; St. Louis, Mo.), hereinafter designated as HEPES, containing approximately 138 mM NaCl, to which was added sufficient KCl to make the [K$^+$] 2, 4, 6, or 8 mM. Fluorescence intensity was measured after eight minutes of equilibration, although actual sensor response time (to changes in the analyte K$^+$ concentration) was rapid (i.e., about 30 to 120 seconds). Results of these measurements are given in Table III.

TABLE III

| Time (min.) | [K$^+$] | Fluorescence Intensity | | |
| --- | --- | --- | --- | --- |
| | | Disk 1 | Disk 2 | Disk 3 |
| 0 | 2 | 724 | 700 | 676 |
| 8 | 4 | 748 | 720 | 695 |
| 16 | 6 | 762 | 734 | 711 |
| 24 | 8 | 770 | 743 | 720 |
| 32 | 6 | 763 | 736 | 712 |
| 40 | 4 | 748 | 722 | 698 |
| 48 | 2 | 722 | 700 | 678 |

Table III shows that sensors prepared as in Example 19 are reversible with respect to changes in potassium ion concentration which exceed those normally observed during bypass surgery (i.e., 3 to 6 mM).

pH-Dependence

Change in sensor fluorescence intensity as a function of pH of the aforementioned HEPES buffer at K$^+$ concentrations of 2, 4, and 6 mM were measured with a CDI™ S400 monitor. The results of these measurements are given in Table IV.

TABLE IV

| | Sensor Intensity at Various [K$^+$] | | |
| --- | --- | --- | --- |
| pH | 2 mM | 4 mM | 6 mM |
| 7.07 | 356 | 373 | 398 |
| 7.34 | 346 | 366 | 391 |
| 7.48 | 339 | 366 | 386 |

TABLE IV-continued

| | Sensor Intensity at Various [K$^+$] | | |
|---|---|---|---|
| pH | 2 mM | 4 mM | 6 mM |
| 7.69 | 334 | 363 | 385 |
| 7.90 | 326 | 353 | 380 |

Table IV shows that sensors prepared as in Example 19 exhibit small changes in response (to changing [K$^+$]) with changing pH, especially in the physiological pH range. More particularly, change in fluorescence intensity of the sensor at physiological pH range (i.e., about 7.3 to 7.5) and at physiological potassium ion concentrations (i.e., about 4 mM) constitutes about 2% of the total fluorescence change observed from pH=7.07 to pH=7.90. This compares with a pH dependence of about 6% or more for the same coumarocryptand bound to non-PVC matrices and an even larger dependence for the non-immobilized coumarocryptand in an aqueous buffered solution of the same pH range.

Stability

Stability of the sensing composite was measured both in a buffer solution and in blood.

A. Buffer

A 50 mM solution of HEPES containing 138 mM NaCl, as measured by an AVL 9120™ sodium/potassium analyzer (AVL Scientific Corp.; Roswell, Ga.), was maintained at a constant temperature of 24° C. in a Lauda™ RC 20 thermostated water bath (Lauda Dr. R. Wobser GmbH & Co. KG; Germany) and circulated through a sensor loop by means of a model 13400 peristaltic pump (Sarns/3M Health Care; Ann Arbor, Mich.). The pH of the solution, which ranged from 7 to 8, was monitored with an Orion™ pH meter (Orion Research; Cambridge, Mass.). Osmolality of the solution, which ranged from 285 to 305 mOsm, was measured on an Advanced Wide-Range Osmometer 3W2™ (Advanced Instrument Inc.; Needham Heights, Mass.). The [K$^+$] of the buffer solutions was determined with an IL 643™ flame photometer (Instrumental Laboratories; Lexington, Mass.).

Two sets of [K$^+$] "step" experiments were performed (both at room temperature). First, [K$^+$] was alternated between 0 and 8 mM. A sensing composite as described in Example 19 was allowed to equilibrate with the 0 mM KCl solution before being exposed to the 8 mM solution, whereupon the sensing composite was allowed to equilibrate for 5 to 10 minutes at the new [K$^+$] (although complete equilibration was quite rapid). This process was repeated five times over a period of five hours. The fluorescence intensity of both solutions (i.e., approximately 488 counts for the 0 mM solution and approximately 567 counts for the 8 mM solution as measured on a CDI™ S400 monitor) remained virtually unchanged over the length of the experiment.

The second "step" experiment involved [K$^+$] of 3 and 7 mM, which is the concentration range normally encountered in bypass operations, as measured by an IL 643™ flame photometer. A sensing composite was allowed to equilibrate with the 3 mM KCl solution before being exposed to the 7 mM solution, whereupon the sensing composite was allowed to equilibrate for several minutes at the new [K$^+$] (even though complete equilibration occurred within about 90 seconds). This process was repeated five times over a period of about three and one-half hours. The fluorescence intensity for both solutions (i.e., approximately 647 counts for the 3 mM solution and approximately 677 counts for the 7 mM solution as measured on a CDI™ S400 monitor) remained virtually unchanged over the length of the experiment.

B. Blood

Bovine blood was adjusted to a [Na$^+$] of 138 mM and an osmolality of 300 mOsm, as described in the previous section. Potassium ion concentrations of approximately 3 and 9 mM were obtained by addition of KCl, as described previously. Blood pH was maintained at about 7.34±0.02, as measured by an ABL-4™ blood gas analyzer (Radiometer A/S; Copenhagen, Denmark), by continuous sparging with a gas composition of 2.8% $CO_2$, 5.5% $O_2$, 91.7% $N_2$. The blood solutions were stored in a thermostated water bath and, after being introduced into the testing loop, circulated by means of a peristaltic pump. (See previous section.) The sensors were secured to CDI™ S400 cassettes and CDI™ Model 6730 Quik-cell blood gas monitoring units, ⅜ in. size (CDI/3M Health Care).

To alternate the two [K$^+$] solutions, initial sensor intensities were obtained with the 3 mM solution, and the test loop was emptied before the 9 mM solution was introduced directly. When this process was reversed, the test loop was rinsed with a wash solution of blood with [K$^+$]=3 mM to prevent contamination of the 3 mM test solution. (This washing process caused the sensor to be exposed to air between blood solution changes, which resulted in an increase in the sensor response time. It was found that hydrating the sensor in a HEPES buffer solution containing 8 mM K$^+$ and a small amount of a surfactant such as Triton™ X-100 or Tween™ 80 (both available from Aldrich), preferably the latter due to its approval for internal drug applications, produced stable sensor intensities.)

Without using an intermediate wash bath between blood solution changes, the response time (95%) when going from a [K$^+$] of 3 to 9 mM was about 40 seconds and about 65 seconds when going from 9 to 3 mM.

The sensors displayed good stability over a period of about five hours. The intensity produced by the 9 mM solution decreased slightly (i.e., approximately 5 counts) over the course of the testing, but this was believed to be due to dilution of this solution by the 3 mM solution with which it was alternated.

Various modifications and alterations of this invention which do not depart from the scope and spirit of this invention will become apparent to those skilled in the art. This invention should not be unduly limited to the illustrative embodiments set forth herein.

We claim:

1. A fluorescent ionophoric compound having the general formula

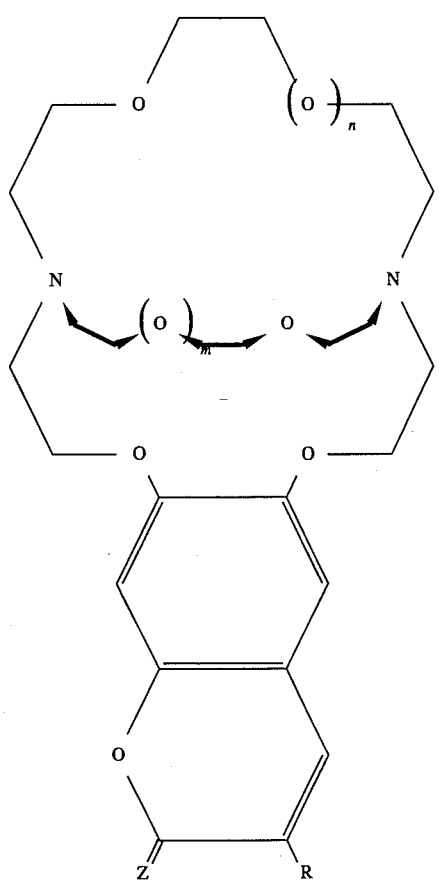

wherein
  m and n are independently 0 or 1,
  R is at least one of an electron withdrawing group and a polarizable group, and
  Z is oxygen or N—R" where R" is H or a $C_1$ to $C_4$ alkyl group,
said compound having an absorbance maximum in the range of 350 to 440 nm.

2. The ionophoric compound of claim 1 wherein R is selected from the group consisting of carboxyl, carboxamide, sulfonylaryl, ester, keto-alkyl ester, and aromatic groups.

3. The ionophoric compound of claim 2 wherein R is a carboxyl group.

4. The ionophoric compound of claim 2 wherein R is an ethyl ester group.

5. The ionophoric compound of claim 2 wherein said keto-alkyl ester group has the formula

6. The ionophoric compound of claim 2 wherein said sulfonylaryl or aromatic group is substituted by a group selected from the class consisting of amine, carboxylic acid, and sulfonic acid groups.

7. The ionophoric compound of claim 2 wherein said aromatic group is selected from the group consisting of phenyl, benzimidazolyl, benzoxazolyl, and benzthiazolyl groups.

8. The ionophoric compound of claim 1 having the formula

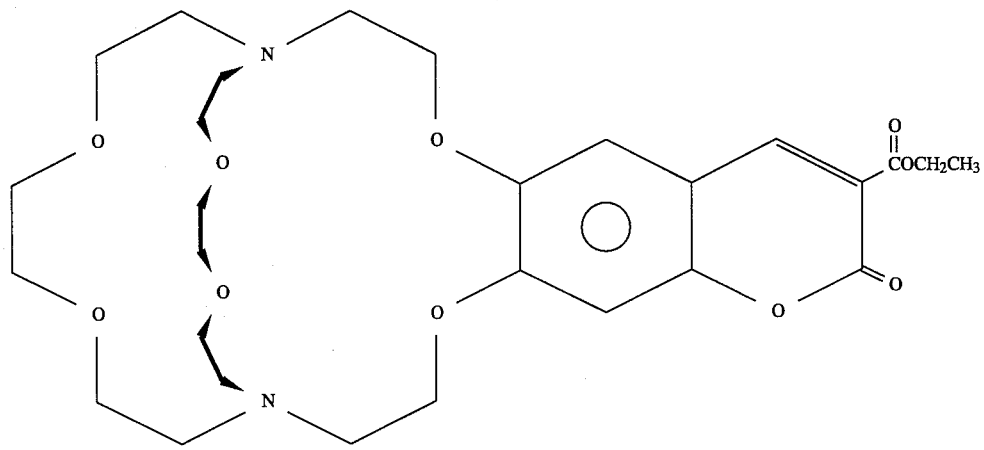

9. A cation-sensing composite structure comprising a substrate and the fluorescent ionophoric compound of claim 1 wherein said compound is covalently bound to said substrate through R, defined as above, by means of one of a bond and a linking group, said linking group comprising functionalities at both ends, the functionality at one end of said linking group being complementary to the functionality of R and the functionality at the other end being complementary to a functional group on said substrate.

10. The sensing composite structure according to claim 9 wherein said functionalities of said linking group are independently selected from the group consisting of amine, amide, ester, oxirane, olefin, urea, silanol, carbamate, isocyanate, thioisocyanate, sulfonamide, sulfonyl chloride, carboxyl, chlorotriazine, hydrazine, hydrazide, and aldehyde groups.

11. The sensing composite structure according to claim 9 wherein said linking group is hydrophilic.

12. The sensing composite structure according to claim 11 wherein said substrate is selectively permeable to protons or the hydronium ion.

13. The sensing composite structure according to claim 12 wherein said sensing composite structure is a pH sensor.

14. The sensing composite structure according to claim 9 wherein said linking group comprises a longest chain including 5 to 125 carbon or hetero atoms.

15. The sensing composite structure according to claim 14 wherein said longest chain of said linking group comprises 10 to 70 carbon or hetero atoms.

16. The sensing composite structure according to claim 9 wherein said substrate is hydrophilic.

17. The sensing composite structure according to claim 9 wherein said substrate comprises a polymeric material.

18. The sensing composite structure according to claim 17 wherein said polymer is coated on a membrane.

19. The sensing composite structure according to claim 18 wherein said coated polymer is selected from the group consisting of polyvinylchloride, copolymers and terpolymers of polyvinylchloride, copolymers of styrene and at least one of maleic acid and maleic anhydride, copolymers of polyalkylvinylether and at least one of maleic acid and maleic anhydride, polymers and copolymers of vinyldimethyl azlactone, and copolymers of one of acrylate esters, methacrylate esters, acrylamides, and methacrylamides with one of acrylic acid and methacrylic acid.

20. The sensing composite structure according to claim 18 wherein said membrane is hydrophilic porous polypropylene.

21. The sensing composite structure according to claim 17 wherein said polymeric material comprises silica.

22. The sensing composite structure according to claim 17 wherein said polymeric material possesses a net negative charge.

23. The sensing composite structure according to claim 9 wherein said substrate is substantially planar in shape.

24. The sensing composite structure according to claim 9 wherein said composite structure is a powder.

25. The sensing composite structure according to claim 24 wherein said powder is adhered to a surface which is substantially planar.

* * * * *

UNITED STATES PATENT AND TRADEMARK OFFICE
CERTIFICATE OF CORRECTION

PATENT NO.: 5,474,743
DATED: December 12, 1995
INVENTOR(S): John E. Trend, Cary A. Kipke, Mitchell A. Rossman, Masao Yafuso and Sanjay L. Patil It is certified that error appears in the above-identified patent and that said Letters Patent is hereby corrected as shown below:

Col. 2, line 9    Before "4,822,746" insert -- U.S. Pat. No. --

Col. 13, line 33   "ionophores" should read -- Ionophores --

Col. 15, line 22   "102°14 102.5° C." should read -- 102° - 102.5° C. --

Col. 15, line 54   "1M" should read -- 1 M --

Col. 18, line 40   "$0.05 \leq A_{max}23$" should read -- $0.05 \leq A_{max} \leq$ --

Signed and Sealed this

Tenth Day of September, 1996

Attest:

BRUCE LEHMAN

Attesting Officer    Commissioner of Patents and Trademarks